United States Patent [19]

Harris et al.

[11] Patent Number: 5,252,714

[45] Date of Patent: Oct. 12, 1993

[54] PREPARATION AND USE OF POLYETHYLENE GLYCOL PROPIONALDEHYDE

[75] Inventors: J. Milton Harris; M. R. Sedaghat-Herati, both of Huntsville, Ala.

[73] Assignee: The University of Alabama in Huntsville, Huntsville, Ala.

[21] Appl. No.: 618,882

[22] Filed: Nov. 28, 1990

[51] Int. Cl.⁵ .................. C07K 3/08; C07C 321/14; C07C 47/12; C07C 43/10
[52] U.S. Cl. .................. 530/391.9; 106/287.23; 106/287.24; 106/287.25; 525/515; 530/391.7; 530/406; 530/410; 568/41; 568/494; 568/613
[58] Field of Search ............... 424/85.8; 530/350, 387, 530/389, 402, 812, 815, 391.7, 391.9, 406, 410; 514/2, 12; 526/273, 289; 568/41, 494, 613, 623, 57; 528/421, 380; 106/287.23, 287.24, 287.25, 287.26, 287.32; 525/512, 513, 515

[56] References Cited

U.S. PATENT DOCUMENTS

| | | | |
|---|---|---|---|
| 4,002,531 | 1/1977 | Roger | 435/188 |
| 4,029,765 | 6/1977 | Hetting | 424/92 |
| 4,101,380 | 7/1978 | Rubinstein et al. | 530/410 |
| 4,179,337 | 12/1979 | Davis et al. | 435/181 |
| 4,791,192 | 12/1988 | Nakagawa et al. | 530/406 |
| 5,080,891 | 1/1992 | Saifer et al. | 435/180 |

OTHER PUBLICATIONS

Veronese et al., J. Pharm. Pharmacol., vol. 35, pp. 757–758 (1983).

*Primary Examiner*—Jeffrey E. Russel
*Attorney, Agent, or Firm*—Oblon, Spivak, McClelland, Maier & Neustadt

[57] ABSTRACT

A new polyethylene glycol derivative (PEG) having the property of not being destroyed by water and also being able to retain reactivity in water and selectively react with amine groups. Also provided is a process for modifying organic or polymer surfaces in water by connecting PEG derivatives to exposed amine groups which provides a process whereby there is efficient linking to organic or polymer surfaces in water by use of the PEG derivatives.

19 Claims, No Drawings

PREPARATION AND USE OF POLYETHYLENE GLYCOL PROPIONALDEHYDE

BACKGROUND OF THE INVENTION

1. Field of the Invention

This invention relates generally to polyethylene glycol derivatives (PEGs), their fabrication and use, and more particularly to their use in aqueous environments and even more particularly to their use in aqueous environments to modify other substances such as proteins or surfaces.

2. Description of the Background

PEGs are neutral, hydrophilic polymers that are also soluble in water and a variety of organic solvents, and which possess a wide array of biomedical and biotechnical applications. Once in aqueous solution they are heavily hydrated, highly mobile and exclude other polymers (including proteins and nucleic acids). As a consequence PEGs are nontoxic, nonimmunogenic, and capable of forming aqueous two-phase systems with a variety of polymers. Molecules coupled to PEG become nontoxic, nonimmunogenic, soluble in water and many organic solvents, and surfaces modified by PEG attachment become hydrophilic and protein rejecting. These properties have led to a variety of biotechnical and biomedical applications including: aqueous two-phase partitioning, protein (i.e., enzyme, antibody, antigen) immobilization, drug modification, and preparation of protein rejecting surfaces. In addition, PEG-coated surfaces can be used to control wetting and electroosmosis. The properties of PEG mentioned above are described in the following papers which are hereby incorporated by reference: B. J. Herren, S. G. Slater, J. M. Van Alstine, J. M. Harris, and R. S. Snyder, *J. Colloid Interface Sci.*, 51, 46-55 (1987); and J. M. Harris, D. E. Brooks, J. F. Boyce, R. S. Snyder, and J. M. Van Alstine, in "Dynamic Aspects of Polymer Science" J. D. Andrade, Ed., Plenum 1988 pp. 111-119.

Preparation of new activated PEGs has become central to many studies on PEG applications as shown by J. M. Harris in *J. Macromol. Sci.-Rev. Macromol. Chem. Phys.*, C25, 325-373 (1983) which is hereby incorporated by reference. Typically, useful PEGs contain at least one electrophilic center available for reaction with nucleophilic centers of biomolecules (e.g., lysine, cysteine and like residues of proteins) or surfaces (e.g., aminated glass). A variety of active PEGs have been prepared, yet there is continued interest in synthesis of new derivatives possessing properties not now available. A property of particular interest is increased selectivity, including relative inertness toward water and high reactivity toward desired functional groups. As an example, PEG tresylate, a much used derivative, is reactive toward a variety of nucleophiles including water, while PEG aldehydes are inert toward water and react primarily with amines. Inertness toward water is desired, not only because of efficiency of storage, preparation, and application, but also because it permits stepwise linkage, in aqueous media, of molecules to surfaces and molecules to molecules.

Preparation of activated and selective PEGs mentioned above are provided in the following references which are hereby incorporated by reference: K. Yoshinaga and J. M. Harris, *J. Bioact. Comp. Polym.*, 1, 17-24 (1989); K. Nilsson and K. Mosbach, *Methods in Enzymology*, 104, 56 (1984); C. Delgado, G. E. Francis, and D. Fisher, in "Separations Using Aqueous Phase Systems," D. Fisher and I. A. Sutherland, Eds., Plenum, London, 1989, pp. 211-213; M.-B. Stark and J. K. Holmberg, *Biotech. Bioeng.*, 34, 942 (1989); J. M. Harris and K. Yoshinaga, *J. Bioact. Compat. Polym.*, 4, 281 (1989); H. Walter, D. E. Brooks, and D. Fisher (Editors), "Partitioning in Aqueous Two-Phase Systems," Academic Press, Orlando, Fla., 1985; D. Fisher and I. A. Sutherland (Editors), "Separations Using Aqueous Phase Systems: Applications in Cell Biology and Biotechnology," Plenum, London, 1989.

U.S. Pat. No. 4,002,531 (1977) describes a preparation of PEG acetaldehyde for attaching PEG to enzymes and other proteins. However, the subsequently published article by Harris mentioned above, indicates that the preparation as described in the U.S. Pat. No. 4,002,531 gives very little of the desired aldehyde. More importantly, PEG acetaldehyde is unstable in the presence of base and of limited utility for protein or surface modification in water as shown by M. S. Paley and J. M. Harris, in *J. Polym. Sci. Polym. Chem. Edn.*, 25, 2447-2454 (1987).

U.S. Pat. No. 4,179,337 (1979) to Davis et al indicates that PEG can be attached to proteins (such as enzymes and insulin) to provide PEG-protein conjugates which are soluble and nonimmunogenic. Several uses for these nonimmunogenic PEG-proteins are described and claimed. Also a wide variety of methods for attaching PEG to proteins to provide soluble PEG-protein conjugates are described and claimed. Each of the Davis et al methods for attaching PEG to proteins uses conventional, water-sensitive PEGs.

SUMMARY OF THE INVENTION

An object of this invention is to provide a new PEG derivative which is not destroyed by water, retains reactivity in water, and selectively reacts with amine groups.

Another object of this invention is to provide a process for modifying organic or polymer surfaces in water by connecting PEG derivatives to exposed amine groups.

Yet another object of this invention is to provide a process for efficiently linking or tethering molecules to organic or polymer surfaces in water by use of PEG derivatives.

Yet another object of the invention is to provide a PEG derivative which selectively reacts with amine groups.

These objects of the invention are achieved by preparing and using a novel compound or its chemical equivalents: PEG Propionaldehyde. PEG propionaldehyde is stable in water and selectively reacts with amine groups in water. The reaction of the amine and the aldehyde produces an imine which can easily be reduced to form a stable amine bond. PEG propionaldehyde reacted in such a manner maintains a second aldehyde group away from the amine containing site or surface. This second aldehyde group can be used to tether another amine containing material.

The ideal PEG derivative is: (1) reactive with nucleophilic groups (typically amino) on proteins and surfaces; (2) stable in aqueous media and on the shelf; (3) easily prepared and characterized; and (4) capable of coupling to proteins without reducing protein activity. Many of these properties are potentially possessed by PEG aldehydes. In particular, aldehydes are in equilibrium with their hydrates in water, and will react in this medium with amines to form imines (which can be reduced in situ with sodium cyanoborohydride). The availability of aqueous coupling chemistry has several benefits. For example, surfaces can be modified that either dissolve or soften deleteriously in organic solvents. Secondly, PEG aldehydes can potentially be used for tethering molecules to surfaces in water. To do this, PEG can be first coupled to the surface, in water, and then reacted in a second step still in water, to some other molecule such as a protein. Previous activated PEGs cannot be used in this fashion since they react with water too rapidly to permit the two-step process. A second potential benefit is that the aldehyde reacts only with amino groups and not with other nucleophilic centers.

As a consequence, synthesis of PEG aldehydes has been actively pursued. As a first attempt PEG acetaldehyde (PEG-O-CH$_2$CHO) was prepared. This compound has proven useful in some cases and is the subject of the Royer patent mentioned above, however reproducible results are difficult to achieve. Closer examination showed that the compound is very sensitive to decomposition in aqueous base, presumably by aldol condensation. If aldol condensation is the decomposition route then more desirable derivatives would be the benzaldehyde derivative and the propionaldehyde derivative. The benzaldehyde derivative was prepared but it proved too unreactive to be of general use.

DESCRIPTION OF THE PREFERRED EMBODIMENTS

A new PEG aldehyde (i.e., PEG propionaldehyde or: I) possessing unique properties is presented. This novel PEG fits into a class of PEG derivatives which could be described as "active" PEGs because they are chemically active and ready for chemical attachment to other molecules and surfaces. There are many active PEGs, and their prime applications are in attachment of PEG to proteins and surfaces to alter the properties of the proteins and surfaces in a desirable way. Shown below are the formula for PEG and PEG propionaldehyde:

Polyethylene Glycol (or PEG)

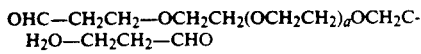

PEG Propionaldehyde Compound I (or OHC—PEG—CHO)

USE OF PEG PROPIONALDEHYDE OR EQUIVALENTS

The prime characteristic of the present novel derivative I is that it is not destroyed by water. As shown in equations 1 and 2, compound I exists in water in equilibrium with its hydrate, and it reacts readily with amino groups present on other molecules. The imine that forms can be further reduced (e.g., with sodium cyanoborohydride or sodium borohydride) to give an amine.

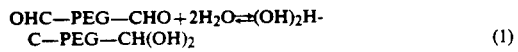 (1)

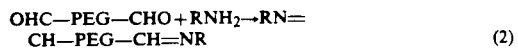 (2)

This property of retention of reactivity in water is not possessed by any other active PEG derivative. This property is an extremely valuable one since it permits chemical modification of other substances in water without concern for loss of activity during reaction. It should be noted that it is frequently necessary to conduct these modification procedures in water because the substance to be modified (e.g., a protein or an organic polymer such as a plastic) may be harmed by a water-free organic solvent. At present, other active but water-sensitive PEGs are used for reaction in water with the understanding that a significant loss of active PEG will result. As described below, this loss of activity has serious consequences.

Two applications serve to illustrate the value of retention of chemical reactivity in water.

First, this property means that one can modify other substances (such as proteins or surfaces) in water with great efficiency (an economic benefit); i.e., no by-product is produced from reaction of activated PEG with water.

Secondly, water stability means that this active PEG I can be used to link or tether molecules to organic-polymer surfaces in water. Several works have shown that PEG is an unusually effective linker for tying active molecules onto surfaces (see for example references by H. A. Jacobs, T. Ohano, and S. W. Kim in *J. Biomed. Mat. Res.*, 23, 611 (1989); S. Nagaoka, H. Murumatani, Y. Oyori, and H. Tanazawa, *J. Bioact. Compt. Polym.*, 4, 323 (1989) which are hereby incorporated). However, application of this process is presently limited to surfaces that tolerate water-free organic solvents. With the water insensitive compound I, one can first link I to the surface in water (thus avoiding water-free organics that will damage many surfaces) through one reactive group at one end of the PEG chain, and then subsequently couple a molecule to the remaining reactive aldehyde group at the other end of the PEG chain, as shown in Scheme I. There is no loss of activity of the "remaining aldehyde group" during the first step as there would be with currently available active PEGs. More typical activated PEGs cannot be used in this fashion since they react with water too rapidly to permit the two-step process.

Scheme I

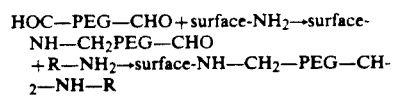

We will not go into the potential applications for this linking technology, but suffice it to say that many exist (see for example articles by M. B. Stark, J. M. Harris, mentioned above and also: H. A. Jacobs, T. Okano, and S. W. Kim, *J. Biomed. Mat. Res.*, 23, 611 (1989); and S. Nagaoka, H. Kurumatani, Y. Mori, and H. Tanazawa, *J. Bioact. Compt. Polym.*, 4, 323 (1989) which are hereby incorporated by reference.

Less important than water stability, but still of significance are two other chemical properties of the aldehyde. First the aldehyde reacts only with amines and this gives desired selectivity. Second, reduction of the first-formed imine intermediate gives a stable amine coupling linkage that could be of advantage relative to previously available linkages, for long term applications.

PREPARATION OF PEG PROPIONALDEHYDE OR EQUIVALENTS

To obtain a reactive PEG aldehyde, which is resistant to aldol decomposition, we have prepared PEG-propionaldehyde (PEG—CH$_2$CH$_2$CHO, I). The compound can be prepared by reaction of the diethyl acetal of 3-chloropropionaldehyde with PEG alkoxide followed by hydrolysis (yield about 50%). A more effective route to the chemically equivalent sulfur analog is as follows (in DMSO):

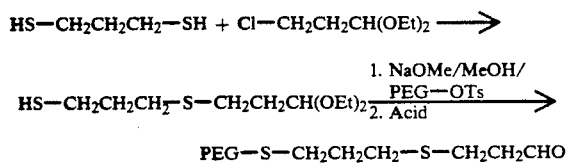

Proton NMR is useful for identifying compound I. The intermediate acetal gives the following spectrum (in DMSO): 1.11 ppm, 6H, t, methyls; 1.77 ppm, 4H, m, —CH$_2$—CH$_2$—CH$_2$—; 2.54 ppm, m, 6H, —CH$_2$S—; 3.50 ppm, —O—CH$_2$—; 4.55 ppm, t, 1H, acetal CH. And the final product gives the spectrum (in DMSO): 1.78 ppm, t, 2H, —CH$_2$—CH$_2$—CH$_2$—; 2.54 ppm, 8H, m, CH$_2$S, 2.73 ppm, t, 2H, CH$_2$—CHO; 3.51 ppm, m, —O—CH$_2$—, backbone, 9.64 ppm, 1H, s,—CHO.

It should be noted that many other syntheses of compound I can be devised. The presence of sulfur atoms in the prepared analog of I is not of chemical importance; i.e., no observed chemical difference exists between the compounds with sulfur substituted for oxygen in the chain. Similarly, it is to be expected that many related PEG aldehydes can be devised which will prove chemically equivalent. For instance, compounds which are hetero-substituted with Se, Te, N, or P at the O site, and those with a hydrocarbon group attached to the carbon adjacent to the oxygen site, should be chemically equivalent. Compounds with the general formula:

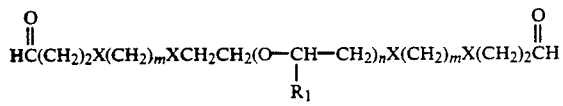

where R$_1$ is H or a C$_1$ to C$_6$ alkyl, and X is O, S, Se, Te, or NR$_2$ where R$_2$ is H or a C$_1$ to C$_6$ alkyl, should be chemically equivalent to PEG propionaldehyde.

In sharp contrast to PEG-acetaldehyde, compound I is stable in the presence of mild base, and, in contrast to PEG-benzaldehyde, compound I is highly reactive in forming the imine from methyl amine. Reaction of I with methylamine in DMSO at room temperature is complete (as shown by proton NMR) within 5 minutes. Imine formation is reversible in this case, and sodium cyanoborohydride should be added to give reductive amination.

Compound I is ideal for protein modification. Reductive amination proceeds rapidly under a variety of conditions. In a typical preparation we react about three mg of I for every mg of protein, along with a slight excess of cyanoborohydride, for one hour at room temperature in pH 9 borate buffer, followed by dialysis against phosphate-buffered saline; high pH is utilized to avoid reduction of aldehyde. Under these conditions we find that 30-40% of the available lysines are modified, and we find that partitioning of the modified protein in a two-phase system is dramatically shifted. Two examples follow. The antibody against alkaline phosphatase (anti-alkaline phosphatase) is 38% modified under these conditions, and the modified protein partitions (in a system consisting of 8% dextran T-40, 6% PEG 8000, 0.15 M NaCl, 0.010 M sodium phosphate, pH 7.2) 99% to the top phase; unmodified protein partitions 90% to the bottom phase. Similarly, the antibody against human red blood cells (anti-human RBCs) is 28% modified under these conditions, and the modified protein partitions (in a system consisting of 4.55% dextran T-500, 3.86% PEG 8000, 0.15 M NaCl, 0.010M sodium phosphate, pH 7.2) 43% to the top phase; unmodified protein partitions almost entirely to the bottom phase. Compound I readily attaches to glass and polymethylmethacrylate, which have been aminated. These same surfaces can then effectively bind proteins.

So in summary, PEG-propionaldehyde I is much more reactive toward amines than PEG-benzaldehyde, stable in water, stable to base, and reactive with lysine groups of proteins (i.e., reductive amination).

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A compound, as described by formula (I):

$$R_1(CH_2)_2X(CH_2)_mX(CH_2)_2(O—CHCH_2)_nX(CH_2)_mX(CH_2)_2R_3 \quad \text{I}$$
$$\underset{R_2}{|}$$

wherein R$_1$ and R$_3$ each independently consist of an element selected from the group consisting of

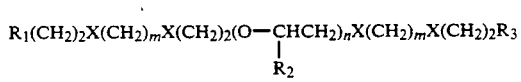

R$_4$—N=CH, and R$_4$—NH—CH$_2$, wherein R$_4$ is an antibody; and wherein X is selected from elements of the group consisting of O, and S; and wherein R$_2$ is a C$_1$ to C$_6$ alkyl, or H, and;

wherein n is an integer, and n less than 10,000, and m is an integer selected from the group consisting of 2, 3, 4, 5, or 6.

2. A compound, as recited in claim 1, wherein R$_1$ and R$_3$ are

X is an element selected from the group consisting of O and S, and R$_2$ is H, m=2 or 3.

3. A composition comprising a compound as recited in any of claims 1 or 2, further comprising water.

4. A compound, as recited in any one of claims 1, or 2, wherein n is between 10 and 1,000.

5. A process for amine modifications comprising the steps of:

preparing an amine comprising substance in a solution and adding a compound, I,

I:

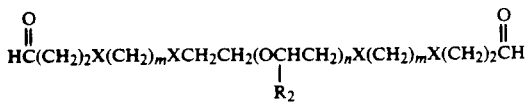

wherein X=O or S, n<10,000, and $R_2$ is a $C_1$ to $C_6$ alkyl, or H, and m is an integer selected from an element of the group consisting of 1, 2, 3, 4, 5, or 6.

6. A process for amine modification as recited in claim 5, further comprising the steps of:
   waiting for a period of time sufficient for said compound to react with said amine comprising substance to form a final product;
   separating said product from unreacted substance.

7. A process for amine modification, as recited in claim 5 or 6, wherein said amine comprising substance is essentially a protein.

8. A process for amine modification, as recited in claim 5 or 6, wherein said solution is water based.

9. A process for amine modification, as recited in claim 11 or 12, wherein said solution is buffered and contains enough reducing agent to reduce imine bonds occurring in an intermediate product of said amine comprising and said compound.

10. A process for amine modification, as recited in claim 9, wherein said solution is borate buffered with a pH between 8 and 10, and said reducing agent is cyanoborohydride.

11. A process for amine modification, as recited in claim 5 or 6, wherein said solution is at a temperature between 0 and 100° C.

12. A process for amine modification, as recited in claim 5 or 6, wherein said compound in said solution is present with said amine comprising substance in said solution in a weight ratio of between 1:1 and 10:1.

13. A process for amine modification, as recited in claim 5 or 6, wherein the density of said amine comprising substance in solution is less than 100 grams per liter.

14. A process for amine modification, as recited in claim 7, wherein said protein is an antibody.

15. A process for amine modification, as recited in claim 5 or 6, further comprising the steps of:
   then contacting an aminated surface with said solution;
   then contacting said surface with a second solution which contains

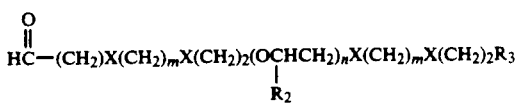

wherein X is selected from an element of the group consisting of O, and S, and n<10,000, and $R_2$ is a $C_1$ to $C_6$ alkyl, or H, and m is an integer selected from an element of the group consisting of 2, 3, 4, 5 or 6, and $R_3$ is selected from an element of the group of $$\begin{matrix} CH, \\ \| \\ O \end{matrix}$$

and $R_4$—NH—$CH_2$, wherein $R_4$ is selected from an element of the group consisting of organic compounds.

16. A process for amine modification, as recited in claim 6, wherein said separating is accomplished by dialysis against a phosphate buffered saline.

17. A process for amine modification, as recited in claim 16, wherein said amine comprising substance is an anti-alkaline phosphatase.

18. A process for amine modification, as recited in claim 16, wherein said substance is an anti-human RBC.

19. A process for amine modification as recited in claim 5 or 6, further comprising the steps of, then adding a second solution to said first solution wherein said second solution contains a second substance which comprises at least one amino group.

* * * * *

UNITED STATES PATENT AND TRADEMARK OFFICE
CERTIFICATE OF CORRECTION

PATENT NO. : 5,252,714
DATED : October 12, 1993
INVENTOR(S) : J. Milton Harris, et. al.

It is certified that error appears in the above-indentified patent and that said Letters Patent is hereby corrected as shown below:

Column 1, after the title, line 3, insert the following paragraph--

This invention was made with Government support under Grant NAGW-812 awarded by the National Aeronautics and Space Administration, Washington, D.C. The Government has certain rights in this invention. --

Signed and Sealed this

Fourth Day of June, 1996

Attest:

Attesting Officer

BRUCE LEHMAN

Commissioner of Patents and Trademarks